United States Patent

Eiermann et al.

(10) Patent No.: US 6,362,381 B1
(45) Date of Patent: Mar. 26, 2002

(54) NITRATION OF AROMATIC HYDROCARBONS

(75) Inventors: Matthias Eiermann, Limburgerhof; Klaus Ebel, Lampertheim, both of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/946,639

(22) Filed: Sep. 6, 2001

(30) Foreign Application Priority Data

Sep. 22, 2000 (DE) .......................................... 100 47 163

(51) Int. Cl.⁷ ............................................ C07C 205/00
(52) U.S. Cl. ........................ 568/939; 568/928; 568/929
(58) Field of Search ................................ 568/927, 928, 568/929, 937, 939

(56) References Cited

U.S. PATENT DOCUMENTS

| | | | | |
|---|---|---|---|---|
| 4,331,819 A | * | 5/1982 | Mc Call | 568/939 |
| 4,417,080 A | * | 11/1983 | Ross et al. | 568/939 |
| 4,465,876 A | * | 8/1984 | Milligan | 568/940 |
| 4,551,568 A | * | 11/1985 | Sato et al. | 568/939 |
| 4,754,083 A | * | 6/1988 | Reith et al. | 568/932 |
| 5,728,901 A | * | 3/1998 | Ramprasad et al. | 568/930 |
| 5,963,878 A | * | 10/1999 | Brereton et al. | 568/927 |
| 6,242,657 B1 | * | 6/2001 | Konig et al. | 568/936 |
| 6,291,726 B1 | * | 9/2001 | Lee et al. | 568/939 |

* cited by examiner

*Primary Examiner*—Jean F. Vollano
(74) *Attorney, Agent, or Firm*—Oblon, Spivak, McClelland, Maier & Neustadt, P.C.

(57) ABSTRACT

Aromatic hydrocarbons are nitrated by a process in which the aromatic hydrocarbon is reacted in the liquid phase with an oxide of nitrogen selected from NO, $N_2O_3$, $NO_2$ and $N_2O_4$ and with an oxygen-containing gas stream in the presence of a heterogeneous oxidic catalyst, wherein at least 0.1 mol %, based on the aromatic hydrocarbon, of water is present at the beginning of the reaction.

10 Claims, No Drawings

NITRATION OF AROMATIC HYDROCARBONS

The present invention relates to a process for nitrating aromatic hydrocarbons.

Aromatic nitro compounds are key intermediates in organic synthesis and occupy an important position in the chemical industry. For example, they are reduced to amines and further reacted to give isocyanates. Thus, nitrobenzene is a starting material for the preparation of aniline, from which methylenediphenyl diisocyanate (MDI), an important building block for the preparation of polyurethane foams, is obtained. Aromatic nitro compounds are furthermore the basis for the preparation of crop protection agents and drug substances, dyes and explosives.

Aromatic nitro compounds are obtained industrially from the corresponding aromatics by nitration with nitrating acid, a mixture of concentrated nitric acid and sulfuric acid. The process has been known since the 19th century. Depending on the concentration, substitution pattern on the aromatic and reaction conditions, one or more nitro groups are introduced on the aromatic. The disadvantage is the production of nitrating acid which is contaminated with organic compounds and has to be disposed of or regenerated by an expensive procedure. There is therefore a need to find economical alternatives to this process which can be implemented on an industrial scale.

WO 99/42433 discloses a process for nitrating aromatic compounds, in which the aromatic compound is reacted with nitrogen dioxide and oxygen under superatmospheric pressure in the presence of a suspended oxide catalyst in an autoclave. An oxygen partial pressure of from 3 to 8 bar is employed. The low conversions in this process are disadvantageous.

It is an object of the present invention to provide an alternative process for nitrating aromatic hydrocarbons which permits high conversions.

We have found that this object is achieved by a process for nitrating an aromatic hydrocarbon, in which said aromatic hydrocarbon in the liquid phase is reacted with an oxide of nitrogen selected from NO, $N_2O_3$, $NO_2$ and $N_2O_4$ and with an oxygen-containing gas stream in the presence of a heterogeneous oxidic catalyst, wherein at least 0.1 mol %, based on the aromatic hydrocarbon to be nitrated, of water is present at the beginning of the reaction.

It was found that the conversion in the nitration with oxides of nitrogen and oxygen is substantially increased if the nitration is initiated in the presence of small amounts of water.

Preferably at least 0.5, particularly preferably at least 1, mol %, based on the aromatic hydrocarbons to be nitrated, of water is employed at the beginning of the nitration.

The water can be used in the liquid phase or in the form of steam. For example, the water can be fed to the reaction as a mixture with the aromatic hydrocarbons to be nitrated, in the liquid phase, or may be fed in separately from these as liquid or as steam. The water can also be used in the form of a water-containing liquid, preferably nitric acid.

The oxide of nitrogen can be used in the liquid phase or as a gas stream containing the oxide of nitrogen. In an embodiment of the invention, liquid dinitrogen tetroxide is used and can be fed to the reaction as a mixture with the aromatics to be nitrated. In a preferred embodiment, the gas stream containing nitric oxide and/or nitrogen dioxide is used. This may contain inert gases, such as nitrogen. Preferably, pure nitrogen dioxide is used.

Oxygen may be used as pure oxygen, diluted with inert gases or in the form of air. Preferably, pure oxygen is used. The use of the pure reaction gases is preferred in the interests of a high reaction rate and small amounts of waste gas.

It is also possible to use industrial mixtures of nitrogen dioxide and oxygen or air, as produced, for example, in the production of nitric acid.

Suitable aromatic hydrocarbons are in general monocyclic or polycyclic aromatic hydrocarbons which may be monosubstituted or polysubstituted by, for example, nitro, nitroso, halogen, hydroxyl, alkoxy, aryloxy, carboxyl, alkylcarbonyloxy, arylcarbonyloxy, acylamino, alkylsulfonyl, arylsulfonyl, alkylsulfoxyl, arylsulfoxyl, sulfo, cyano and/or alkyl groups (above, alkyl is in general $C_1$–$C_{18}$-alkyl), preferably by nitro, halogen, cyano and/or alkyl groups. Amino, alkylamino or dialkylamino groups, low-valency sulfur- or phosphorus-containing substituents and other readily oxidizable or nitratable groups are unsuitable for the purposes of a selective nitration of the aromatic ring. Preferred aromatic hydrocarbons are unsubstituted or substituted benzene, naphthalene, biphenyl, anthracene and phenanthrene.

Of course, mixtures of aromatic hydrocarbons can be employed.

The aromatic hydrocarbon may be nitrated in the form of a pure substance or in solution in a solvent. Suitable solvents are, for example, halohydrocarbons, such as dichloromethane, chloroform, carbon tetrachloride and bromoform, acetonitrile or sluggishly reacting electron-poor aromatic hydrocarbons, such as dinitrobenzene or benzonitrile. Another suitable solvent is nitric acid. Mixtures of different solvents may also be used. Preferably, the procedure is carried out without a solvent or in the nitration product as the solvent.

Suitable oxide catalysts are solid oxygen compounds of one or more elements, selected from elements of the third and fourth main groups and of the third and fourth subgroups (groups IIIa, IVa, IIIb or IVb) of the Periodic Table of the Elements, which compounds are insoluble in the reaction medium. Particularly suitable are oxygen compounds of the silicon, aluminum, zirconium, boron and titanium, which, in their active form, have acidic centers on the catalyst surface. Silicates, borosilicates and aluminosilicates of alkali metals, alkaline earth metals and metals of the fourth subgroup, such as magnesium silicate or titanium silicate, and furthermore zeolites, such as FSM-5, NaY, mordenite or faujasite, may also be used. Naturally occurring materials, such as kaolinite, Fuller's earths or diatomaceous earth, are also suitable.

Preferably, the BET surface area of the catalysts used is at least 50 $m^2/g$. Lower specific surface areas lead to substantially reduced catalytic activity. The catalysts can be prepared, for example, by precipitating suitable precursor compounds, drying and calcination.

Particularly preferred catalysts are silica, lanthanum oxide-doped silica containing up to 10% by weight of $La_2O_3$, kaolinite, NaY zeolite, titanium dioxide and zirconium dioxide.

The novel process can be carried out batchwise or continuously. When effected batchwise, the process can be carried out, for example, in a stirred container under superatmospheric pressure with catalysts suspended in the aromatic hydrocarbon to be nitrated. The oxide of nitrogen can be initially taken as liquid dinitrogen tetroxide together with the aromatic hydrocarbon or can be forced in with the oxygen-containing gas stream as a gaseous oxide of nitrogen, preferably nitrogen dioxide. Water or the water-containing liquid can be initially taken in the liquid phase or forced in as steam. The disadvantage of the discontinuous procedure, however, is the high catalyst abrasion and the constantly changing process parameters, such as pressure, temperature and composition of the reaction mixture. The changing process conditions make it more difficult to operate batchwise reactors safely, so that they often have to be classified in the highest explosion protection class, owing to the danger of the formation of explosive gas mixtures. The batchwise procedure is therefore less preferred.

The novel process is preferably carried out continuously.

In one embodiment, the liquid mixture, containing one or more aromatic hydrocarbons to be nitrated and, if required, a solvent, is passed, together with the gas stream containing the oxide of nitrogen and the oxygen, water or steam over a fixed catalyst bed. The liquid phase is passed cocurrently or countercurrently to the gas phase over the fixed catalyst bed, for example by the trickle-bed or liquid phase procedure. Suitable reactors are, for example, tubular reactors or tube-bundle reactors.

Where there is sufficient density difference between catalyst and reaction medium and a sufficient sedimentation rate, it is also possible to keep the solid catalyst suspended in the ascending liquid phase of a reaction tube and to carry out a catalyst separation via a sedimentation zone at the top of the reactor or a filter apparatus.

Reaction columns in which the catalyst bed is present in suitable retaining apparatuses, in the case of tray columns, for example, on column trays, are also suitable. It is also possible to use continuously operated kettles or kettle cascades which are equipped with circulation means, such as stirrers or circulation pumps.

In all processes, the required amount of water can be fed to the reactor in pure form or in the form of water-containing liquid, such as nitric acid, together with the aromatic (mixture) or separately therefrom as a liquid, or as steam together with or separately from the other reaction gases.

Preferably, a fixed catalyst bed is employed in the trickle-bed procedure.

The novel process is carried out in the presence of a solid catalyst phase, a liquid starting material phase and a gas phase containing two reactants. As a combination of a nitration and an oxidation reaction, the novel nitration as a whole is particularly dependent on the reaction rates of the individual steps. The cooperation of absorption and desorption processes in gas phase and liquid phase and the individual reaction steps can be described kinetically only with difficulty. Nevertheless, the novel process can surprisingly be carried out over a fixed catalyst bed or a fluidized catalyst bed with residence time and mixing behavior differing considerably from that in a stirred kettle.

The pressure and temperature are chosen so that a sufficient reaction rate results. This also depends on the reactivity of the aromatic compound to be nitrated. Although as a rule a reaction is observed even at atmospheric pressure with air, in general an oxygen partial pressure of at least 2 bar is employed in order, for example, to nitrate compounds of medium reactivity, such as benzene or naphthalene. High pressures of up to 300 bar are possible but are less preferred for economic reasons. Oxygen partial pressures of from 2 to 25 bar in the case of aromatics of medium and low reactivity are preferred.

The temperature and residence time are chosen as a function of the reactivity. Aromatics of medium reactivity, such as benzene and naphthalene, can be nitrated at as low as room temperature, the procedure preferably being effected at from 40 to 80° C. with residence times of from 10 minutes to 5 hours. Aromatics of low reactivity, such as nitrobenzene or benzonitrile generally require temperatures of from 60 to 180° C. and residence times of from 30 minutes to 20 hours. The latter also applies to multiple nitrations.

We claim:

1. A process for nitrating an aromatic hydrocarbon, in which the aromatic hydrocarbon in the liquid phase is reacted with an oxide of nitrogen selected from NO, $N_2O_3$, $NO_2$ and $N_2O_4$ and with an oxygen-containing gas stream in the presence of a heterogeneous oxidic catalyst, wherein at least 0.1 mol %, based on the aromatic hydrocarbon, of water is present at the beginning of the reaction.

2. A process as claimed in claim 1, wherein water is used in the liquid phase or in the form of steam.

3. A process as claimed in claim 1, wherein water is used in the form of a water-containing liquid.

4. A process as claimed in claim 3, wherein water is used in the form of aqueous nitric acid.

5. A process as claimed in claim 1, wherein an oxide of nitrogen in the liquid phase or in the form of a gas stream containing the oxide of nitrogen is used.

6. A process as claimed in claim 1, wherein oxygen in the form of pure oxygen or in the form of air is used.

7. A process as claimed in claim 1, wherein the aromatic hydrocarbon is initially taken in solution in a solvent.

8. A process as claimed in claim 1, wherein the catalyst is an oxygen compound of one or more elements of groups IIIa, IVa, IIIb or IVb.

9. A process as claimed in claim 1, wherein the aromatic hydrocarbon is a mono- or polycyclic aromatic hydrocarbon which is unsubstituted or monosubstituted or polysubstituted by nitro, $C_1$–$C_{18}$-alkyl, cyano or halogen substituents and is selected from the group consisting of unsubstituted or substituted benzene, naphthalene, biphenyl, anthracene and phenanthrene.

10. A process as claimed in claim 1, wherein the process is carried out continuously over a fixed catalyst bed by the liquid-phase or trickle-bed procedure.

* * * * *